United States Patent [19]

Rosenthal et al.

[11] Patent Number: 5,362,966

[45] Date of Patent: Nov. 8, 1994

[54] MEASUREMENT OF FINGER TEMPERATURE IN NEAR-INFRARED QUANTITATIVE MEASUREMENT INSTRUMENT

[76] Inventors: Robert D. Rosenthal; Lynn N. Paynter; Reynaldo J. Quintana, all c/o Futurex, P.O. Box 2398, Gaithersburg, Md. 20886

[21] Appl. No.: 103,758

[22] Filed: Aug. 10, 1993

Related U.S. Application Data

[63] Continuation-in-part of Ser. No. 813,739, Dec. 30, 1991, Pat. No. 5,237,178, which is a continuation-in-part of Ser. No. 565,302, Aug. 10, 1990, Pat. No. 5,077,476, which is a continuation-in-part of Ser. No. 544,580, Jun. 27, 1990, Pat. No. 5,086,229.

[51] Int. Cl.⁵ .................................. G01N 21/35
[52] U.S. Cl. ......................... 250/341.1; 128/633

[58] Field of Search ............... 250/339, 340, 341; 128/633, 664

[56] References Cited

U.S. PATENT DOCUMENTS 4,882,492  11/1989  Schlager ...................... 250/341
5,267,152  11/1993  Yang et al. .................. 250/341

Primary Examiner—Paul M. Dzierzynski
Assistant Examiner—Richard Honig
Attorney, Agent, or Firm—Rothwell, Figg, Ernst & Kurz

[57] ABSTRACT

A near-infrared quantitative analysis instrument for measuring blood analytes in a finger of a subject includes a temperature-sensing thermistor-type ring worn around the base of the finger and connected to the instrument via a cable. A light shield glove may be provided with the thermistor-type ring attached thereto.

11 Claims, 4 Drawing Sheets

MEASUREMENT OF FINGER TEMPERATURE IN NEAR-INFRARED QUANTITATIVE MEASUREMENT INSTRUMENT

CROSS-REFERENCE TO RELATED APPLICATIONS

This application is a continuation-in-part of copending application Ser. No. 07/813,739, filed Dec. 30, 1991, now U.S. Pat. No. 5,237,178 which is a continuation-in-part of Ser. No. 07/565,302, filed Aug. 10, 1990, now U.S. Pat. No. 5,077,476, which is a continuation-in-part of patent application Ser. No. 07/544,580, filed Jun. 27, 1990, now U.S. Pat. No. 5,086,229.

BACKGROUND OF THE INVENTION

Field of the Invention and Background

This invention relates to instruments for the noninvasive quantitative measurement of constituents in blood, such as blood glucose levels. Specifically, this invention relates to an improved analysis instrument utilizing an improved measurement of the temperature of the body part, typically a finger, which is being irradiated with near-infrared energy for measurement of the blood analyte levels.

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions. In U.S. Pat. No. 5,077,476, incorporated by reference herein, it is taught that noninvasive blood glucose measurement can be made by transmitting near-infrared light through an extremity of the body, e.g., the most distal portion of the index finger. The temperature of the body at the point of measurement can be an important parameter because the peak wavelengths for near-infrared light passing through water (the human body is approximately 67% water) shift as a function of temperature. Thus, a means to insure that the shift in peak wavelength as a function of temperature does not interfere with the analyte measurement is important.

In the aforementioned '476 patent, the finger temperature can be taken into account as a separate term in a linear regression algorithm used in a near-infrared measurement instrument such as represented by the following equation:

$$C = K_0 + K_1[\log 1/I_A - \log 1/I_B]/[\log 1/I_D - \log 1/I_E] + K_2 T_S + K_3 T_A$$

wherein C is the analyte concentration, $K_0$ through $K_3$ are calibration constants, $T_S$ is the local surface temperature of the finger and $T_A$ is the temperature of the air within the instrument, and the log 1/I terms represent optical density values at particular near-infrared wavelengths A, B, D and E. The calibration constants can be generated by various regression techniques such as multiple linear regression, stepwise regression, partial least squares fitting, principle component analysis, etc.

FIG. 1 illustrates a near-infrared blood analyte measurement instrument as disclosed in the '476 patent. Briefly, up to six or more IREDs (Infrared Emitting Diodes) represented in the figure by IREDs 5 and 6, detector 8 and processing means 10 are contained within a lightweight hand-held housing unit 1. Illustrative IREDs 5 and 6 are separated by light baffle 4 and are positioned so that the near-IR energy is directed through window 14, which may be light scattering, and onto the skin of the test subject. Optical filters, illustrated at 16 and 17, are positioned between each IRED and the window 14 for filtering the near-IR energy, thereby optimizing the band of near-IR energy striking the subject. It is very important that the test subject's fingertip not be exposed to ambient light. Further, it is desirable that the actual measurement be made near the rear of the finger nail. Finger stop 30 illustrated in FIG. 1 facilitates properly positioning the test subject's finger. FIG. 1 also illustrates a finger retainer 2 to securely position the user's finger inside the instrument and to provide sufficient blockage of ambient light. Spring 21 pushes the finger retainer 2 against the bottom of the test subject's finger thereby providing a secure fit. Linear potentiometer 19 is connected to finger retainer 2 and can measure an individual's finger thickness. In addition, an inflatable diaphragm or rubber/foam iris (illustrated at 15) is used to secure the test subject's finger and shield light.

FIG. 1 illustrates that when the finger is inserted into chamber 28, a built-in thermistor 29 measures the finger's temperature. A second thermistor 27 is positioned inside the analytical instrument 1 for measuring the ambient air temperature therein. The ambient air temperature measurement could be made at any time prior to the instrument's actual use, but preferably at the time the optical standard is measured. As shown in FIG. 1, the thermistor 29 is disposed near the optical measurement point of detector 8. While such an approach may be feasible, it raises complex engineering problems in that the location for the temperature measuring device is very close to the optical measurement path of the optical sensor. The resultant crowding of these two separate measurement devices can cause errors in either or both of the optical measurement and the temperature measurement.

SUMMARY OF THE INVENTION

The present invention solves the above-mentioned problems by providing an alternate approach that achieves the same accuracy in temperature measurement as the previous approach, while eliminating any errors caused by crowding of components. Specifically, the present invention provides a near-infrared quantitative analysis instrument for noninvasive measurement of blood present in a body part of a subject, comprising introducing means including a near-infrared energy source for introducing near-infrared energy into blood present in a body part of a subject, detecting means for detecting near-infrared energy being emitted from said body part and producing signals in response thereto, positioning means for positioning said body part closely adjacent to both said introducing means and said detecting means, housing means for housing said introducing means, said detecting means and said positioning means, temperature sensing means for measuring the temperature of said body part at a location on said body part external to said housing means; and processing means responsive to the signals produced by said detecting means and the temperature measured by said temperature sensing means for generating a signal indicative of a quantity of a certain analyte in the blood present in said body part.

DETAILED DESCRIPTION OF THE PREFERRED EMBODIMENTS

According to one embodiment of the invention utilizing near-IR transmission analysis techniques, near-IR light energy at bandwidths centering on one or more wavelengths of interest is transmitted through a blood-containing portion of the body of a test subject. In a preferred embodiment, the near-IR bandwidth is from 600–1100 nm, and preferably 600–1000 nm. The near-IR energy emerges from the test subject, generally opposite from the near-IR source, and is detected by a detector. Following amplification of the detector-generated signal, the amplified output is processed into an output signal indicating the amount of glucose in the subject's blood.

Figure 2:
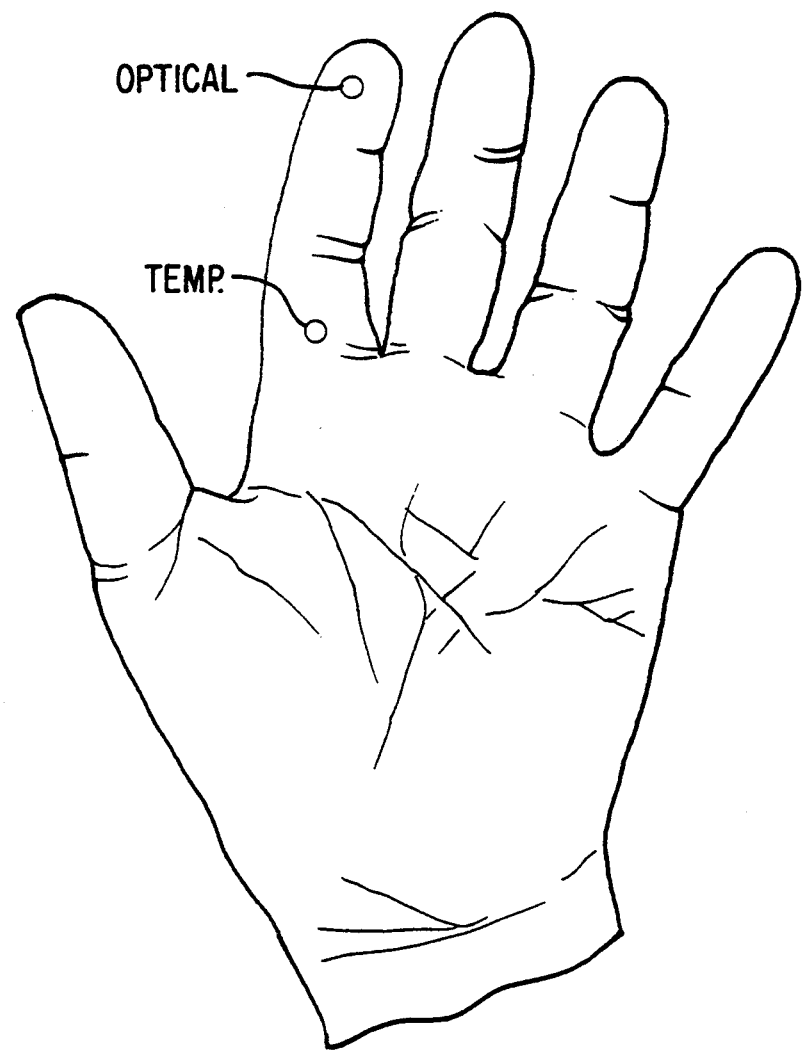
FIG. 2 illustrates positions on the finger of a test subject for making temperature measurements and optical measurements, respectively.

It has been discovered by the present inventors that temperature measurement made at the base portion of the finger most proximate the palm of the hand is directly related to the temperature at the tip or distal portion of the finger at which an optical near-infrared measurement is taken by the instrument. These points are shown in FIG. 2.

Figure 3:
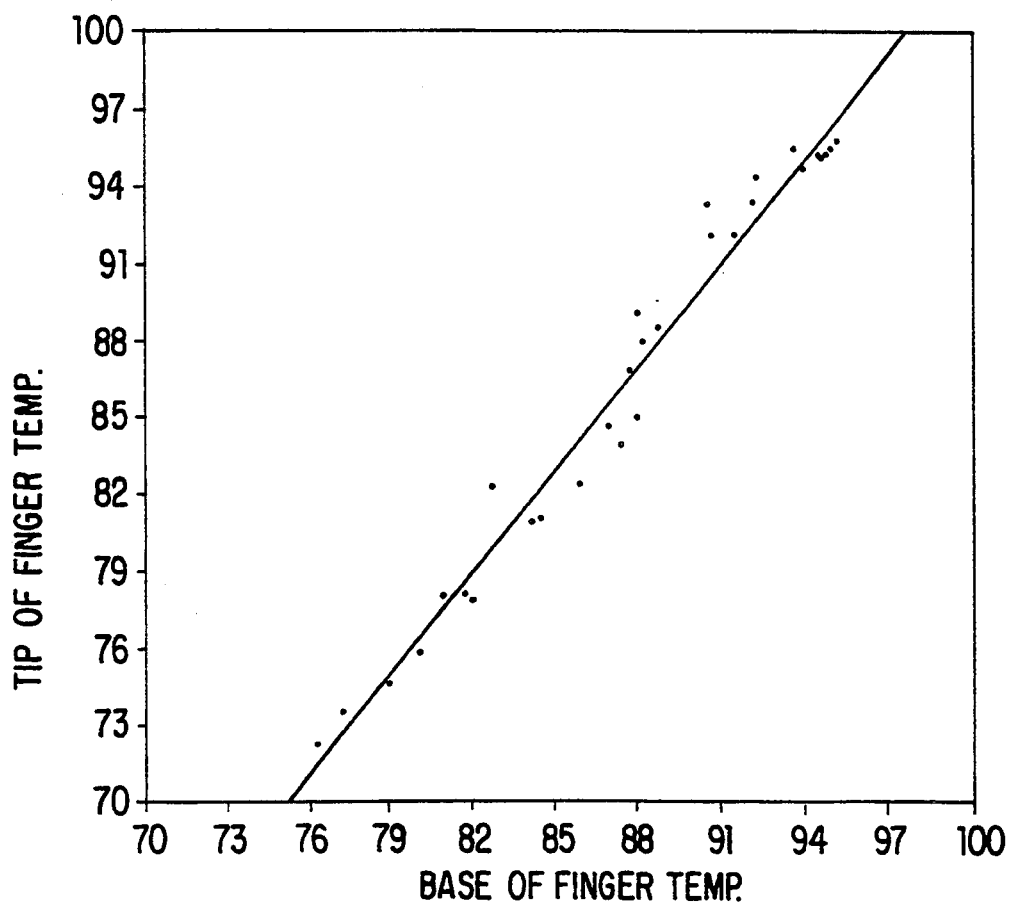
FIG. 3 illustrates a graph of a linear function representing the relationship between the surface temperature at the base of the finger and the surface temperature at the tip or distal end portion of the finger.

FIG. 3 illustrates the results of an experimental test during which the temperature at the base of the finger and the temperature at the tip of the finger were measure simultaneously over a certain range of room temperatures. For the test, a styrofoam piece was loosely wrapped around the base of the left index finger, and another styrofoam piece was loosely wrapped around the tip of the left index finger to simulate the conditions to which the finger would be subjected in a noninvasive blood glucose measurement in the measurement instrument, i.e., the tip of the finger would be somewhat shielded from room air. The pieces of styrofoam were used at the base and tip to simulate the test apparatus.

The temperature at the base of the finger and the tip of the finger were measured in 5 to 10 minute intervals over an approximately six hour period with a thermistor placed against the underside of the base of the finger and against the approximate location used for near-infrared measurement in the instrument. The thermistor was held against the portions of the finger for 15 seconds for stabilization purposes and then the temperature was recorded. Base and tip measurements were each repeated twice, with the resultant three temperature measurement values being averaged for each time interval measurement. Room temperature was also recorded. Table I displays the time, room temperature, and average tip and base temperature for each measurement.

TABLE I

| Sample # | Time | Room Temp. | Base Temp. | Tip Temp. |
|---|---|---|---|---|
| 1 | 8:45 | 73.4 | 95.2 | 95.8 |
| 2 | 9:00 | 72.9 | 93.8 | 94.5 |
| 3 | 9:15 | 70.8 | 92.3 | 93.5 |
| 4 | 9:30 | 70.5 | 90.7 | 92.2 |
| 5 | 9:45 | 69.8 | 92.9 | 93.4 |
| 6 | 9:55 | 69.8 | 88.1 | 89.1 |
| 7 | 10:10 | 70.3 | 91.6 | 92.2 |
| 8 | 10:30 | 70.7 | 88.0 | 85.0 |
| 9 | 10:35 | 71.0 | 87.4 | 83.9 |
| 10 | 10:40 | 71.6 | 86.0 | 82.3 |
| 11 | 10:47 | 71.1 | 84.3 | 80.9 |
| 12 | 10:55 | 70.8 | 81.8 | 78.1 |
| 13 | 11:10 | 73.9 | 81.0 | 78.1 |
| 14 | 11:15 | 75.5 | 82.8 | 82.2 |
| 15 | 11:20 | 76.9 | 90.6 | 93.3 |
| 16 | 11:25 | 76.4 | 94.1 | 94.8 |
| 17 | 11:35 | 77.4 | 95.3 | 95.9 |
| 18 | 11:40 | 77.4 | 95 | 95.5 |
| 19 | 11:55 | 75.2 | 93.7 | 95.5 |
| 20 | 12:00 | 76.4 | 94.6 | 95.4 |
| 21 | 12:05 | 76.1 | 93.4 | 94.3 |
| 22 | 12:15 | 76.0 | 94.5 | 95.4 |
| 23 | 12:25 | 75.3 | 94.2 | 95.1 |
| 24 | 1:30 | 73.8 | 95.0 | 95.5 |
| 25 | 1:40 | 76.1 | 94.8 | 95.4 |
| 26 | 1:50 | 72.0 | 94.7 | 95.1 |
| 27 | 2:00 | 71.3 | 88.3 | 88.0 |
| 28 | 2:05 | 68.3 | 88.8 | 88.5 |
| 29 | 2:12 | 72.3 | 87.0 | 84.6 |
| 30 | 2:17 | 71.2 | 87.8 | 86.8 |
| 31 | 2:25 | 70.9 | 84.6 | 81 |
| 32 | 2:35 | 71.3 | 82.1 | 77.9 |
| 33 | 2:40 | 68.3 | 80.1 | 75.9 |
| 34 | 2:47 | 70.9 | 79 | 74.6 |
| 35 | 2:53 | 71.5 | 77.3 | 73.5 |
| 36 | 3:00 | 67.9 | 76.4 | 72.3 |

The 35 averaged data points are shown in FIG. 3. This figure illustrates that there exists a strong relationship between the temperature at the base and tip of the finger, with a correlation constant of 0.99. The absolute mean difference between the two locations is 1.8° F. As indicated by the results, at warmer room temperatures the tip of the finger was approximately 0.9° F. warmer than the base of the finger, and at colder room temperatures the temperature of the tip decreased to approximately 3.4° F. colder than the temperature of the base, apparently confirming the notion that blood flow to the extremities is minimized as environmental temperatures approach colder levels.

A linear regression was performed to obtain the linear function. The line equation is $Y = 1.33X - 29.884$, which indicates that while there is a slope adjustment, there is no statistically significant difference between the temperature of the finger tip and the temperature of the base.

Figure 1:
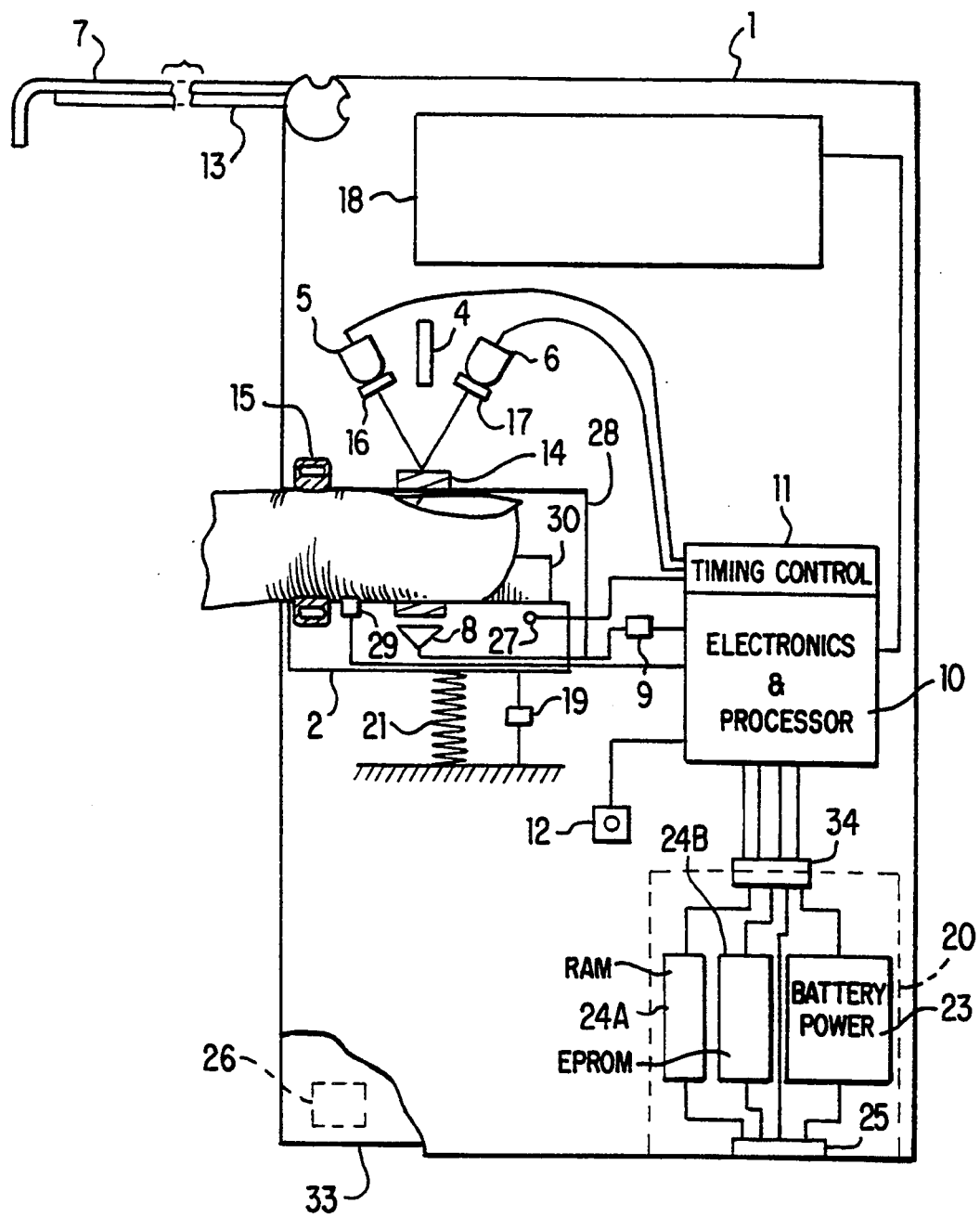
FIG. 1 illustrates a near-infrared blood glucose measurement instrument of the type applicable to the present invention.
Figure 4:
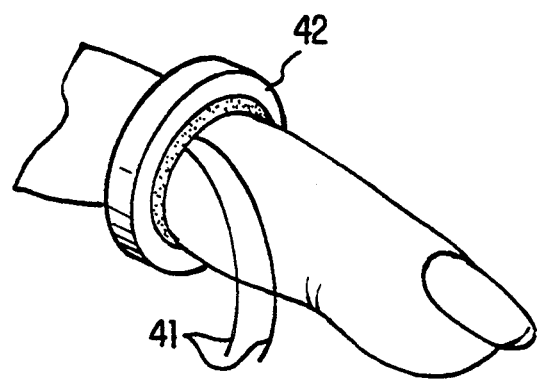
FIG. 4 illustrates a finger-temperature measurement device according to one embodiment of the present invention.

As a consequence of the obtained test results, it has been discovered that the internal thermistor 29 as shown in FIG. 1 can be eliminated and replaced by a simple flexible thermistor ring 42, as shown in FIG. 4. In one embodiment of the invention, the ring is made of a flexible, compressible insulating material (such as rubber) carrying a flexible thermistor material that is fastened to the finger by use of a hook-and-loop-type fastener, commonly recognized as Velcro ®. The fastener allows the thermistor material to press against the skin, yet does not restrict blood flow to the tip of the finger. The thermistor measurement is inputted to the measurement instrument through a flexible cable 41, which can be either permanently attached to the measurement unit or attached to the unit via a connector element. With such an arrangement, the relationship between the temperature measured at the base of the finger and the temperature of the finger tip is linear with a correlation of approximately 0.99. The slope and intercept differences shown in FIG. 3 are automatically taken into account during calibration according to the above-defined equation, i.e., the intercept would be reflected in the constant $K_0$, and the constant $K_1$ would incorporate the slope of the linear function.

Figure 5:
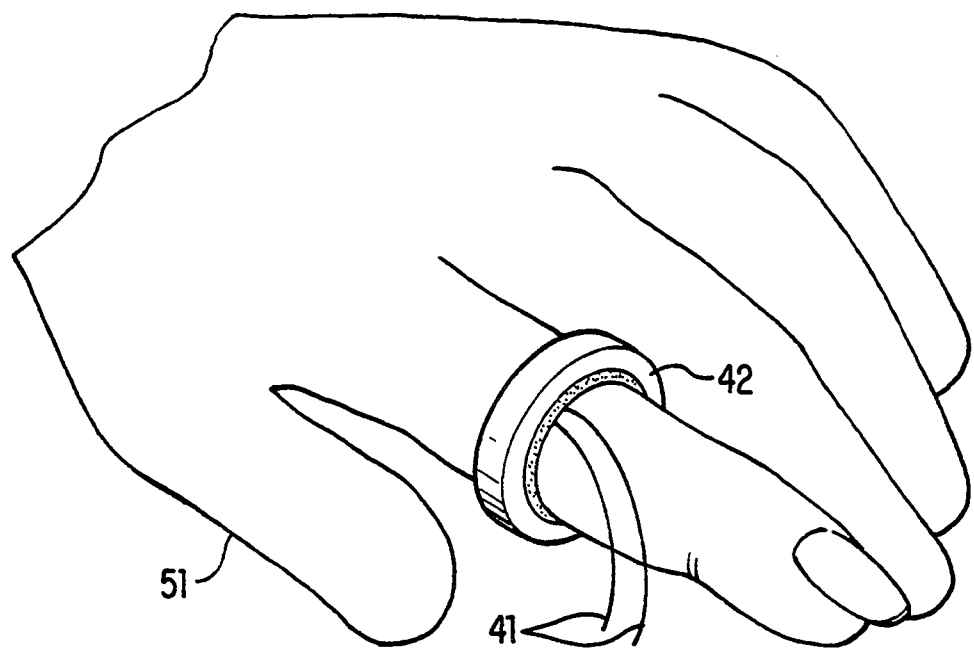
FIG. 5 illustrates a finger-temperature measurement device according to a second embodiment of the present invention.

FIG. 5 shows an alternative embodiment in which the finger temperature measurement device is mounted on and forms part of an opaque light shield glove 51. The light shield glove is used to prevent ambient light from being conducted into the test subject's finger, which would adversely interfere with the near-infrared optical measurement. The light shield glove and mounted temperature device would mate with a key-type interface built into the near-infrared measurement instrument, such that when the shield is properly inserted into the interface, the thermistor is readable and optical measurements can be carried out without interference from outside ambient light.

The invention having been thus described, it will be apparent to those skilled in the art that the same may be varied in many ways without departing from the spirit and scope of the invention. Any and all such modifications are intended to be included within the scope of the following claims.

What is claimed is:

1. A near-infrared quantitative analysis instrument for noninvasive measurement of blood present in a body part of a subject, comprising:
   introducing means including a near-infrared energy source for introducing near-infrared energy into blood present in a body part of a subject;
   detecting means for detecting near-infrared energy being emitted from said body part and producing signals in response thereto;
   positioning means for positioning said body part closely adjacent to both said introducing means and said detecting means;
   housing means for housing said introducing means, said detecting means and said positioning means;
   temperature sensing means for measuring the temperature of said body part at a location on said body part external to said housing means; and
   processing means responsive to the signals produced by said detecting means and the temperature measured by said temperature sensing means for generating a signal indicative of a quantity of a certain analyte in the blood present in said body part.

2. A near-infrared quantitative analysis instrument as set forth in claim 1, wherein said temperature sensing means comprises a flexible thermistor ring attachable to said body part and a cable connectable to said instrument for transmitting a measured temperature to said processing means.

3. A near-infrared quantitative analysis instrument as set forth in claim 2, wherein said body part is a finger.

4. A near-infrared quantitative analysis instrument as set forth in claim 3, wherein said flexible thermistor ring is attachable to a base portion of said finger, and said introducing means introduces near-infrared energy into a tip portion of said finger.

5. A near-infrared quantitative analysis instrument as set forth in claim 1, wherein said body part is a finger, said temperature sensing means comprises a flexible thermistor ring attachable to said finger and a cable connectable to said instrument for transmitting a measured temperature to said processing means, and further comprising a light shielding glove to be worn by said subject to block ambient external light from interfering with said measurement, wherein said flexible thermistor ring is mounted as part of said glove.

6. A near-infrared quantitative analysis instrument as set forth in claim 1, wherein said near-infrared energy is in the range of 600–1100 nm.

7. A flexible thermistor ring attachable to a finger of a subject for measuring the temperature of said finger and including means for outputting the measured temperature, for use with a near-infrared quantitative analysis instrument for noninvasive measurement of an analyte in blood present in said finger.

8. A method of near-infrared quantitative analysis for noninvasive measurement of blood present in a body part of a subject, comprising the steps of:
   inserting said body part into a near-infrared quantitative analysis instrument;
   introducing near-infrared energy into blood present in said body part of said subject;
   detecting near-infrared energy being emitted from said body part and producing signals in response thereto;
   measuring the temperature of said body part at a location on said body part external to said instrument; and
   generating a signal indicative of a quantity of a certain analyte in the blood present in said body part in response to the signals produced by said detecting step and the temperature measured by said temperature measuring step.

9. A method of near-infrared quantitative analysis as set forth in claim 8, wherein said body part is a finger, and said step of measuring the temperature of said body part comprises the steps of attaching a flexible thermistor ring to said finger, connecting said thermistor ring to said near-infrared quantitative analysis instrument, and transmitting said measured temperature to said instrument.

10. A method of near-infrared quantitative analysis as set forth in claim 9, wherein said flexible thermistor ring is mounted as part of a light shield glove worn by said subject to block ambient external light from interfering with said measurement.

11. A method of near-infrared quantitative analysis as set forth in claim 9, wherein the step of attaching comprises attaching said flexible thermistor ring to a base portion of said finger, and said step of detecting comprises detecting near-infrared energy being emitted from a tip portion of said finger.

* * * * *